(12) United States Patent
Dieterle et al.

(10) Patent No.: US 7,019,168 B2
(45) Date of Patent: Mar. 28, 2006

(54) HETEROGENEOUSLY CATALYZED PARTIAL GAS PHASE OXIDATION OF PROPENE TO ACRYLIC ACID

(75) Inventors: Martin Dieterle, Mannheim (DE); Jochen Petzoldt, Mannheim (DE); Klaus Joachim Müller-Engel, Stutensee (DE); Hans Martan, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 209 days.

(21) Appl. No.: 10/465,653

(22) Filed: Jun. 20, 2003

(65) Prior Publication Data

US 2004/0191953 A1   Sep. 30, 2004

(30) Foreign Application Priority Data

Mar. 25, 2003   (DE) ............................... 103 13 209

(51) Int. Cl.
*C07C 51/16* (2006.01)
*C07C 57/02* (2006.01)

(52) U.S. Cl. .................................... 562/545; 562/598

(58) Field of Classification Search ................ 562/545, 562/547, 598
See application file for complete search history.

(56) References Cited

U.S. PATENT DOCUMENTS 4,366,093 A   12/1982   Shiozaki et al.
6,740,779 B1   5/2004   Tenten et al.

FOREIGN PATENT DOCUMENTS

| | | |
|---|---|---|
| DE | 31 13 179 | 1/1982 |
| DE | 199 48 523 | 4/2001 |
| DE | 102 32 482 | 1/2004 |
| EP | 0 257 565 | 8/1987 |
| EP | 0 253 409 | 1/1988 |
| EP | 0 293 224 | 11/1988 |
| EP | 0 990 636 | 4/2000 |
| EP | 199 55 176 | 1/2001 |
| EP | 1 106 598 | 6/2001 |
| WO | WO 00/53557 | 9/2000 |
| WO | WO 01/36364 | 5/2001 |

*Primary Examiner*—Paul A. Zucker
(74) *Attorney, Agent, or Firm*—Oblon, Spivak, McClelland, Maier & Neustadt. P.C.

(57) ABSTRACT

In a process for partially oxidizing propene to acrylic acid in the gas phase under heterogeneous catalysis, a starting reaction gas mixture comprising propene and oxygen and having a specific composition is oxidized in a first reaction stage over a first fixed catalyst bed having a volume-specific activity which is constant or increases in the flow direction and the acrolein-containing product gas mixture of the first reaction stage is subsequently oxidized in a second reaction stage over a second fixed catalyst bed having a volume-specific activity increasing in the flow direction, and the shaped catalyst bodies of both fixed catalyst beds are annular and each have a specific multimetal oxide composition.

27 Claims, No Drawings

HETEROGENEOUSLY CATALYZED PARTIAL GAS PHASE OXIDATION OF PROPENE TO ACRYLIC ACID

The present invention relates to a process for partially oxidizing propene to acrylic acid in the gas phase under heterogeneous catalysis by initially conducting a starting reaction gas mixture 1 comprising propene, molecular oxygen and at least one inert gas and containing the molecular oxygen and the propene in a molar $O_2:C_3H_6O$ ratio of $\geq 1$ in a first reaction stage at elevated temperature over a first fixed catalyst bed (fixed catalyst bed 1)

whose shaped catalyst bodies are annular, whose active composition is at least one multimetal oxide I of the general formula

$$Mo_{12}X^1_a X^2_b X^3_c X^4_d X^5_e O_n \qquad (1),$$

where the variables are defined as follows:

$X^1$=at least one element from the group comprising Bi, Co and Ni, $X^2$=at least one of the two elements W and Nb, $X^3$=at least one of the two elements Fe and Cr, $X^4$=at least one element from the group comprising K, Cs and Sr, $X^5$=at least one element from the group comprising Si, Al and Zr, a=from 5 to 10, b=from $\geq 0$ to 4, preferably from 1 to 4, c=from 2 to 5, d=from 0.02 to 0.15, e=from 0.5 to 4 and n=a number which is determined by the valency and frequency of the elements in I other than oxygen, whose volume-specific activity in the flow direction of the reaction gas mixture over the first fixed catalyst bed is either constant or increases at least once, (continuously, or abruptly or stepwise), and whose active composition does not change over the first fixed catalyst bed, in such a way that the propene conversion on single pass is $\geq 90$ mol % and the accompanying selectivity of acrolein formation and also of acrylic acid by-production together are $\geq 90$ mol %, the temperature of the product gas mixture leaving the first reaction stage is optionally reduced by direct cooling, or by indirect cooling, or by direct and indirect cooling, secondary gas is optionally added to the product gas mixture in the form of molecular oxygen, or inert gas, or molecular oxygen and inert gas, and the product gas mixture is afterwards conducted as the starting reaction gas mixture 2 comprising acrolein, molecular oxygen and at least one inert gas and containing the molecular oxygen and acrolein in a molar $O_2:C_3H_4O$ ratio of $\geq 0.5$, preferably $\geq 1$, in a second reaction stage at elevated temperature over a second fixed catalyst bed (fixed catalyst bed 2), whose shaped catalyst bodies are annular, whose active composition comprises at least one multimetal oxide II of the general formula

$$MO_{12}V_f X^6_g X^7_h O_m \qquad (II),$$

where the variables are defined as follows:

$X^6$=at least one of the two elements W and Nb, $X^7$=at least one of the elements from the group comprising Sb, Cu, Ni and Fe, f=from 1 to 5, g=from 1 to 2, h=from 1 to 4, and m=a number which is determined by the valency and frequency of the elements in II other than oxygen, whose volume-specific activity in the flow direction of the reaction gas mixture over the second fixed catalyst bed increases at least once (continuously, or abruptly, or stepwise), and whose active composition does not change over the second fixed catalyst bed, in such a way that the acrolein conversion on single pass is $\geq 90$ mol % and the selectivity $S^{AA}$ of the acrylic acid formation assessed over both reaction stages, based on converted propene, is $\geq 80$ mol %.

Acrylic acid is an important monomer which finds use as such or in the form of its acrylic esters to obtain polymers suitable, for example, as adhesives.

The process mentioned at the outset for partial heterogeneously catalyzed gas phase oxidation of propene to acrylic acid is generally known (cf., for example, WO 01/36364).

One objective of such a heterogeneously catalyzed partial gas phase oxidation of propene to acrylic acid is to achieve a very high yield $Y^{AA}$ of acrylic acid (this is the molar ratio of propene converted to acrylic acid, based on the number of moles of propene used), on single pass of the reaction gas mixture through the fixed catalyst bed under otherwise predefined boundary conditions.

A further object of such a heterogeneously catalyzed partial gas phase oxidation of propene to acrylic acid is to achieve a very high space-time yield $STY^{AA}$ of acrylic acid (in a continuous procedure, this is the total amount of acrylic acid obtained per hour and total volume of the fixed catalyst bed used in liters).

Using a given fixed catalyst bed and a given hourly space velocity of propene on the fixed catalyst bed (this refers to the amount of propene in liters at STP (=l STP); the volume in liters that the corresponding amount of propene would take up under standard conditions, i.e. at 25° C. and 1 bar) which is conducted as a constituent of the starting reaction gas mixture 1 per hour through one liter of fixed catalyst bed 1) and also a defined secondary gas stream, the greater is $Y^{AA}$, the greater the space-time yield $STY^{AA}$.

To adjust the hourly space velocity of propene on the fixed catalyst bed, two adjusting screws are available. Firstly, at a given propene content of the starting reaction gas mixture 1, the propene loading can be increased by increasing the hourly space velocity of starting reaction gas mixture 1 on the fixed catalyst bed. However, this measure is disadvantageous in that the pressure drop on passing through the fixed catalyst bed rises with increasing starting reaction gas mixture 1 loading, which requires an increased compressor output.

Alternatively, at a constant starting reaction gas mixture 1 loading, an increase in the propene loading is possible by increasing the proportion of propene in the starting reaction gas mixture 1. However, care has to be taken that, on the one hand, the ratio of molecular oxygen to propene is not too small, since this can impair the quality of the multimetal oxide catalyst used, and that, on the other hand, the explosion limit of the reaction gas mixture along the reaction path is not exceeded (cf., for example, DE-A 10232482).

One way in which the prior art attempts to remedy the latter problem is that the starting reaction gas mixture 1 comprises an added inert diluent gas. In this document, this refers primarily to the gases of which at least 95 mol %, preferably at least 97 mol %, or 99 mol % remain chemically unchanged in the course of the partial oxidation.

The inert diluent gas used by the prior art processes is frequently also cycle gas consisting substantially of nitrogen. This is gas which remains after the product removal (acrylic acid removal) from the product gas mixture of the second reaction stage and is recycled at least in portions to the first reaction stage. When air has been used as the oxygen source, as is frequently customary, it comprises essentially the molecular nitrogen accompanying the molecular oxygen in the air and thus constitutes an inexpensive nitrogen source. However, a disadvantage is that the cycle gas has to be recompressed to the starting pressure of the reaction gas mixture 1 by means of a compressor, in order to compensate for the pressure drop on passing through the fixed catalyst bed. In order to reduce this, annular shaped catalyst bodies are frequently used (cf. DE-A 3113179 and DE-A 19948523).

EP-A 253409 and EP-A 257565 disclose that when an inert diluent gas is used which has a higher molar heat capacity than molecular nitrogen, the proportion of propene in the starting reaction gas mixture 1 can be increased. However, they advise against using steam (which, like molecular nitrogen, is widely and inexpensively available) to an increased extent as such an inert diluent gas, since this is said to generally lead to an increased by-production of acetic acid, even though, in contrast to nitrogen, steam would also have the advantage that it can be brought to the entrance pressure of the starting reaction gas mixture 1 at neutral cost using the waste heat of the exothermic partial gas phase oxidation and, in contrast to the nitrogen from the air, generally occurs as a by-product and is available and does not necessarily have to be recirculated.

Instead, the inert diluent gases recommended by the abovementioned documents are saturated hydrocarbons, as also used in addition to a small amount of steam in WO 01/36364. However, this is disadvantageous in that, in contrast to the nitrogen from the air or the steam which, as already mentioned, generally occurs as a by-product, saturated hydrocarbons are materials of value. The catalysts used in the examples and comparative examples are disclosed neither by EP-A 253409 nor by EP-A 257565.

It is an object of the present invention to increase the yield $Y^{AA}$ of acrylic acid in the process described at the outset without needing an increased compressor output or the use of a material of value as the inert diluent gas, or having to accept increased by-production of acetic acid.

We have found that this object is achieved by a process as defined at the outset, wherein the starting gas reaction mixture 1 is composed of
   from 6 to 15% by volume of propene,
   from 4 to 30% by volume frequently from 6 to 15% by volume of water,
   from $\geq 0$ to 10% by volume (preferably from $\geq 0$ to 5% by volume) of constituents other than propene, water, oxygen and nitrogen, sufficient molecular oxygen that the molar ratio of molecular oxygen present to molecular propene present is from 1.5 to 2.5, and
   and the remainder of molecular nitrogen up to 100% by volume of the total amount.

The reaction temperature in the first reaction stage is frequently from 300 to 380° C. and that in the second reaction stage is frequently from 220 to 310° C.

Similar processes are known from EP-A 990636 and EP-A 1106598. However, a disadvantage of these two documents is that the fixed catalyst beds used are not disclosed.

EP-A 293224 also describes a process which has a certain similarity to the process according to the invention. However, it uses other multimetal oxide compositions, other shaped catalyst bodies and other diluent gases.

According to the invention, preferred multimetal oxides I are those where
   $X^1$=at least one of the two elements Bi and Co,
   $X^2$=at least one of the two elements W and Nb,
   $X^3$=Fe,
   $X^4$=at least one of the two elements K and Cs,
   $X^5$=at least one of the two elements Si and Zr,
   a=from 6 to 8,
   b=from $\geq 0$ to 2.5, preferably from 1 to 2.5,
   c=from 2 to 4,
   d=from 0.04 to 0.1,
   e=from 1 to 3 and
   n=a number which is determined by the valency and frequency of the elements in I other than oxygen.

According to the invention, preferred multimetal oxides II are those where
   $X^6$=at least one of the two elements W and Nb,
   $X^7$=at least one of the elements from the group comprising Cu and Sb,
   f=from 2 to 4,
   g=from 1 to 2,
   h=from 1 to 3, and
   m=a number which is determined by the valency and frequency of the elements in II other than oxygen.

The shaped catalyst bodies supporting both the multimetal oxide active compositions I and the multimetal oxide active compositions II in the process according to the invention may be unsupported catalysts (consist exclusively of the multimetal oxide active composition) or coated catalysts (comprise the multimetal oxide active composition adsorptively applied to an inert support ring). In the process according to the invention, preference is given to using annular unsupported catalysts in the first reaction stage and annular coated catalysts in the second reaction stage.

However, it will be appreciated that the "coated catalyst/unsupported catalyst" or "supported catalyst/supported catalyst" or "coated catalyst/coated catalyst" combinations can also be used in two successive reaction stages. Quite generally, the active composition content in the case of annular coated catalysts, generally both for the first and for the second reaction stage, is from 10 to 30% by weight, preferably from 15 to 25% by weight.

Both in the case of annular coated catalysts and in the case of annular unsupported catalysts, the dimensions of the annular geometry in both reaction stages are preferably:
   from 2 to 11 mm for the external annular diameter,
   from 2 to 11 mm for the annular length and
   from 1 to 5 mm for the wall thickness of the ring.

According to the invention, in the case of annular coated catalysts, preference is given to those (especially for the second reaction stage) whose support rings have a length of from 2 to 10 mm (or from 3 to 6 mm), an external diameter of from 2 to 10 mm (or from 4 to 8 mm) and a wall thickness of from 1 to 4 mm (or from 1 to 2 mm). Very particularly preferably, the support rings have a geometry 7 mm×3 mm×4 mm (external diameter×length×internal diameter). The thickness of the catalytically active oxide composition applied as a coating to the annular support bodies in the process according to the invention is normally from 10 to 1000 µm. Preference is given to from 50 to 500 µm, particular preference to from 100 to 500 µm and very particular preference to from 150 to 250 µm.

According to the invention, in the case of annular unsupported catalysts, preference is given to those (especially for the first reaction stage) whose internal diameter is from 0.1 to 0.7 times the external diameter and whose length is from 0.5 to 2 times the external diameter.

Advantageous unsupported catalyst rings which are suitable according to the invention (especially for the first reaction stage) have an external diameter of from 2 to 10 mm (or from 3 to 7 mm), an internal annular diameter of at least 1.0 mm, a wall thickness of from 1 to 2 mm (or at most 1.5 mm) and a length of from 2 to 10 mm (or from 3 to 6 mm). Frequently, in the case of unsupported catalyst rings suitable according to the invention (especially for the first reaction stage), the external diameter will be from 4 to 5 mm, the internal diameter from 1.5 to 2.5 mm, the wall thickness from 1.0 to 1.5 mm and the length from 3 to 6 mm.

In other words, unsupported hollow cylinder catalyst geometries suitable according to the invention (especially for the first reaction stage) are the geometries (each external diameter×height×internal diameter): 5 mm×3 mm×2 mm; 5 mm×2 mm×2 mm; 5 mm×3 mm×3 mm; 6 mm×3 mm×3 mm and 7 mm×3 mm×4 mm.

Particularly suitable shaped catalyst bodies for the first reaction stage of the process according to the invention are the example having the running No. 3 from DE-A 19855913 (stoichiometry: $Mo_{12}Co_7Fe_3Bi_{0.6}K_{0.08}Si_{1.6}O_x$) as an unsupported hollow cylinder (annular) catalyst of geometry 5 mm×3 mm×2 mm or 5 mm×2 mm×2 mm (each external diameter×length×internal diameter), example 1 from DE-A 10046957 (stoichiometry: $[Bi_2W_2O_9 \times 2\ WO_3]_{0.5}[Mo_{12}Co_{5.5}Fe_{2.94}Si_{1.59}K_{0.08}O_x]_1$) as an unsupported hollow cylinder (annular) catalyst of geometry 5 mm×3 mm×2 mm or 5 mm×2 mm×2 mm (each external diameter×length×internal diameter), and also the coated catalysts 1, 2 and 3 from DE-A 10063162 (stoichiometry: $Mo_{12}Bi_{1.0}Fe_3Co_7Si_{1.6}K_{0.08}$), but applied as annular coated catalysts of appropriate coating thickness and to support rings of geometry 5 mm×3 mm×1.5 mm or 7 mm×3 mm×1.5 mm (each external diameter×length×internal diameter).

Particularly suitable shaped catalyst bodies for the second reaction stage of the process according to the invention are the coated catalysts S1 (stoichiometry: $Mo_{12}V_3W_{1.2}Cu_{2.4}O_n$) and S7 (stoichiometry: $Mo_{12}V_3W_{1.2}Cu_{1.6}Ni_{0.8}O_n$) from DE-A 4442346 having an active composition content of 27% by weight and a coating thickness of 230 μm, the coated catalyst from example 5 of DE-A 10046928 (stoichiometry: $Mo_{12}V_3W_{1.2}Cu_{2.4}O_n$) having an active composition content of 20% by weight, the coated catalysts according to examples 1 to 5 from DE-A 19815281, except, like the aforementioned coated catalysts for the second reaction stage, applied to support rings of geometry 7 mm×3 mm×4 mm (external diameter×length×internal diameter) having an active composition content of 20% by weight (based on the total mass of the coated catalyst), and also a coated catalyst having a biphasic active composition of stoichiometry $(Mo_{10.4}V_3W_{1.2}O_x)(CuMo_{0.5}W_{0.5}O_4)_{1.6}$, preparred according to DE-A 19736105 and having an active composition content of 20% by weight, applied to the aforementioned 7 mm×3 mm×4 mm support.

The shaped catalyst bodies recommended for the second reaction stage are also suitable for the second reaction stage when everything is retained but only the support geometry is changed to 5 mm×3 mm×1.5 mm. The multimetal oxides II can also be used in the second reaction stage in the form of the corresponding unsupported catalyst rings.

The annular catalyst supports used for annular coated catalysts for the first reaction stage and for annular coated catalysts for the second reaction stage are advantageously supports of steatite, more preferably of surface-roughened, substantially nonporous steatite, as produced, for example, by Ceramtec (steatite C220) in DE. Preference is given to using a low-alkali steatite.

Otherwise, annular multimetal oxide I and multimetal oxide II shaped catalyst bodies to be used in accordance with the invention are known from the prior art and can be prepared as described, for example, in WO 01/36364.

The multimetal oxide I and the multimetal oxide II active compositions may have either a monophasic or else a multiphasic construction (cf., for example, DE-A 10046957 and DE-A 10046928 and prior art cited therein).

According to the invention, preference is given to using starting reaction gas mixtures 1 for the process according to the invention which are composed of
  from 7 to 11% by volume of propene,
  from 6 to 12% by volume of water,
  from $\geqq 0$ to 5% by volume of constituents other than propene, water, oxygen and nitrogen,
  sufficient molecular oxygen that the molar ratio of molecular oxygen present to propene present is from 1.6 to 2.2,
  and a remainder of molecular nitrogen up to 100% by volume of the total amount.

The abovementioned is true in particular when the process according to the invention is carried out without using any secondary gas.

To prepare the fixed catalyst bed 1 in the process according to the invention, it is possible to use only shaped catalyst bodies having multimetal oxide active compositions or else substantially homogeneous mixtures of shaped catalyst bodies having multimetal oxide active compositions and shaped bodies (inert diluent bodies) which have no multimetal oxide active composition and behave substantially inertly with respect to the heterogeneously catalyzed partial gas phase oxidation. Useful materials for such shaped inert bodies are in principle all those which are also suitable as support material for coated catalysts suitable according to the invention. Useful materials of this type include, for example, porous or nonporous aluminum oxides, silicon dioxide, thorium dioxide, zirconium dioxide, silicon carbide, silicates such as magnesium silicate or aluminum silicate or the already mentioned steatite.

The geometry of such inert shaped diluent bodies may in principle be as desired. In other words, they may, for example, be spheres, polygons, solid cylinders or else, like the shaped catalyst bodies having active composition, rings. According to the invention, preference is given to selecting those shaped diluent bodies whose geometry corresponds to that of the shaped catalyst bodies diluted by them (the above statements also apply to the homogeneous mixtures of shaped catalyst bodies having multimetal oxide composition and shaped diluent bodies which can be used to prepare the fixed catalyst bed 2).

It is essential to the invention that the chemical composition of the active composition used does not change over the fixed catalyst bed 1. In other words, although the active composition used for an individual shaped catalyst body may be a mixture of different multimetal oxides I, the same mixture then has to be used for all shaped catalyst bodies of the shaped catalyst bed 1.

The volume-specific (i.e. normalized unit of the volume) activity can be reduced in a simple manner by homogeneously diluting a basic amount of shaped catalyst bodies prepared in a uniform manner with shaped diluent bodies. The higher the proportion of shaped diluent bodies, the lower the active composition, i.e. catalyst activity, in a certain volume of the bed.

A volume-specific activity increasing at least once in the flow direction of the reaction gas mixture over the fixed catalyst bed 1 can therefore be attained for the process according to the invention in a simple manner, for example, by beginning the bed with a high proportion of inert shaped diluent bodies based on one type of shaped catalyst bodies, and then either continuously reducing or at least once or more than once abruptly (for example stepwise) reducing this proportion of shaped diluent bodies in the flow direction. When the proportion of shaped diluent bodies is kept constant or no shaped diluent bodies are used at all in the fixed catalyst bed 1, this results in a constant volume-specific activity in the flow direction of the reaction gas mixture over the fixed catalyst bed 1. An increase in the volume-specific activity is also possible, for example, by increasing the thickness of the active composition layer applied to the support at a constant geometry and active composition type of a coated shaped catalyst body or, in a mixture of coated catalysts having the same geometry but having different proportions by weight of active composition, increasing the proportion of shaped catalyst bodies having the higher active composition proportion by weight. A similar effect can also be achieved, for example, by varying the mixing ratio in mixtures of unsupported catalysts and coated catalysts (in the case of identical active composition) in a corresponding manner. It will be appreciated that the variants described can also be applied in combination.

Normally, the volume-specific activity in the process according to the invention will increase not once either within the fixed catalyst bed 1 or within the fixed catalyst bed 2 in the flow direction of the reaction gas mixture.

Downstream and/or upstream of the fixed catalyst bed 1 may be disposed beds consisting exclusively of inert material (for example only shaped diluent bodies) (in this document, they are not included in the definition of the fixed catalyst bed 1, since they contain no shaped bodies which have multimetal oxide active composition). The shaped diluent bodies used for the inert bed may have the same geometry as the shaped catalyst bodies used in the fixed catalyst bed 1. However, the geometry of the shaped diluent bodies used for the inert bed may also be different for the abovementioned geometry of the shaped catalyst bodies (for example spherical instead of annular).

According to the invention, the fixed catalyst bed 1 in the process according to the invention is structured in the flow direction of the reaction gas mixture as follows:

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed catalyst bed 1, a homogeneous mixture of shaped catalyst bodies and shaped diluent bodies (both preferably having substantially the same geometry) having a proportion by weight of shaped diluent bodies (the densities by mass of shaped catalyst bodies and of shaped diluent bodies generally differ only slightly) of normally from 5 to 40% by weight, or from 10 to 40% by weight, or from 20 to 40% by weight, or 25 to 35% by weight. According to the invention, this first zone of the fixed catalyst bed 1 is advantageously followed up to the end of the length of the fixed catalyst bed 1 (i.e., for example, to a length of from 2.00 to 3.00 m, preferably from 2.50 to 3.00 m) by a bed of shaped catalyst bodies diluted only to a slighter extent (than in the first zone) or, most preferably, an unaccompanied (undiluted) bed of the same shaped catalyst bodies which have also been used in the first zone. The abovementioned is true in particular when the shaped catalyst bodies in the fixed catalyst bed 1 are unsupported catalyst rings or coated catalyst rings (in particular those which are mentioned in this document as being preferred). For the purposes of the abovementioned structuring, both the shaped catalyst bodies and the shaped diluent bodies in the process according to the invention advantageously substantially have the annular geometry 5 mm×3 mm×2 mm (external diameter×length×internal diameter).

In a manner corresponding to that in which the volume-specific activity of the fixed catalyst bed 1 can be varied, the volume-specific activity of the fixed catalyst bed 2 can also be varied. Downstream and/or upstream of the actual fixed catalyst bed 2 can again be disposed an appropriate inert bed. However, a constant volume-specific activity within the fixed catalyst bed 2 (as is possible in accordance with the invention within the fixed catalyst bed 1) is excluded in the process according to the invention.

According to the invention, preference is given in the process according to the invention to the fixed catalyst bed 2 being structured in the flow direction of the reaction gas mixture as follows.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed catalyst bed 2, a homogeneous mixture of shaped catalyst bodies and shaped diluent bodies (both preferably having substantially the same geometry) having a proportion by weight of shaped diluent bodies (the densities by mass of shaped catalyst bodies and of shaped diluent bodies generally differ only slightly) of normally from 10 to 50% by weight, preferably from 20 to 45% by weight and more preferably from 25 to 35% by weight. According to the invention, this first zone of the fixed catalyst bed 2 is advantageously followed up to the end of the length of the fixed catalyst bed 2 (i.e., for example, to a length of from 2.00 to 3.00 m, preferably from 2.50 to 3.00 m) by a bed of shaped catalyst bodies diluted only to a slighter extent (than in the first zone) or, most preferably, an unaccompanied bed of the same shaped catalyst bodies which have also been used in the first zone.

The abovementioned applies in particular when the shaped catalyst bodies used in the fixed catalyst bed 2 are coated catalyst rings (in particular those which are listed in this document as being preferred). For the purposes of the abovementioned structuring, both the shaped catalyst bodies or their support rings and the shaped diluent bodies in the process according to the invention advantageously have substantially the ring geometry 7 mm×3 mm×4 mm (external diameter×length×internal diameter).

From an application point of view, the first reaction stage of the process according to the invention can be advantageously carried out, for example, in a tube bundle reactor charged with the fixed catalyst bed 1 (and also optionally upstream and/or downstream inert beds), as described, for example, in EP-B 700714.

In other words, in the simplest manner, the abovementioned charge is disposed in the individual metal tubes of the tube bundle reactor and a temperature medium is conducted around the metal tubes (one-zone method), generally a salt melt. Salt melt and reaction gas mixture can be conducted in simple cocurrent or countercurrent. However, the salt melt (the heating medium) can also be conducted around the tube bundle in a meandering manner when viewed over the reactor, so that a cocurrent or countercurrent to the flow direction of the reaction gas mixture exists only when viewed over the entire reactor. The flow rate of the heating medium (heat exchange medium) is typically such that the temperature rise (caused by the exothermicity of the reaction) of the heat exchange medium from the entry point into the reactor to the exit point from the reactor is from $\geq 0$ to 10° C., frequently from $\geq 2$ to 8° C., often from $\geq 3$ to 6° C. The entrance temperature of the heat exchange medium into the tube bundle reactor is generally from 300 to 360° C., frequently from 300 to 340° C.

Useful heat exchange media are in particular fluid heating media. It is particularly advantageous to use melts of salts such as potassium nitrate, potassium nitrite, sodium nitrite and/or sodium nitrate, or of low-melting metals such as sodium, mercury or else alloys of different metals.

Customarily, the catalyst tubes in the abovementioned tube bundle reactors are manufactured from ferritic steel and typically have a wall thickness of from 1 to 3 mm. Their internal diameter is (in particular when using the annular geometries specified in this document) generally from 20 to 30 mm, frequently from 21 to 26 mm. Their length is typically from 2 to 4 m, frequently from 2.5 to 3.5 m. According to the invention, normally at least 60%, frequently at least 75% of this length are occupied by the fixed catalyst bed 1. From an application point of view, the number of catalyst tubes accommodated in the tube bundle vessel is advantageously at least 5 000, preferably at least 10 000. Frequently, the number of catalyst tubes accommodated in the reaction vessel is from 15 000 to 30 000. Tube bundle reactors having more than 40 000 catalyst tubes form the exception. Within the vessel, the catalyst tubes are normally distributed homogeneously, and the distribution is advantageously selected in such a way that separation of the central internal axes on immediately adjacent catalyst tubes (known as the catalyst tube pitch) is from 35 to 45 mm (cf., for example, EP-B 468290). A tube bundle reactor suitable for the process according to the invention is also disclosed by DE-A 10131126, DE-A 10137768, DE-A 10135498 and DE-A 10232967.

Advantageously, the starting reaction gas mixture 1 is fed to a fixed catalyst bed 1 preheated to the reaction temperature. A bed of inert material preceding a fixed catalyst bed, for example, may serve this purpose.

It will be appreciated that the first reaction stage of the process according to the invention may also be carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out the first reaction stage of the process according to the invention.

In other words, in the simplest manner, the fixed catalyst bed 1 (possibly with upstream and/or downstream inert beds) to be used in accordance with the invention is disposed in the metal tubes of a tube bundle reactor and two substantially spatially separated heating media, generally salt melts, are conducted around the metal tubes. According to the invention, the tube section over which the particular salt bath extends represents a reaction zone. In other words, in the simplest manner, for example, a salt bath A flows around that section of the tubes (reaction zone A) in which the propene is oxidatively converted (on single pass) until a conversion in the range from 40 to 80 mol % is achieved and a salt bath B flows around the section of the tubes (reaction zone B) in which the propene is subsequently oxidatively converted (on single pass) until a conversion value of at least 90 mol % is achieved (if required, the reaction zones A,B to be used in accordance with the invention may be followed by further reaction zones which are maintained at individual temperatures).

From an application point of view, the first reaction stage of the process according to the invention advantageously includes no further reaction zones. In other words, the salt bath B advantageously flows around the section of the tubes in which the propene is subsequently oxidatively converted (on single pass) up to a conversion value of $\geq 90$ mol %, or $\geq 92$ mol % or $\geq 94$ mol % or more.

Typically, the beginning of reaction zone B is beyond the heating point maximum of reaction zone A. The heating point maximum of reaction zone B is normally below the heating point maximum temperature of reaction zone A.

According to the invention, the two salt baths A,B can be conducted in cocurrent or in countercurrent through the space surrounding the reaction tubes relative to the flow direction of the reaction gas mixture flowing through the reaction tubes. It will be appreciated that a cocurrent can also be applied in reaction zone A and a countercurrent in reaction zone B (or vice versa) in accordance with the invention.

It will be appreciated that in all of the abovementioned configurations within a particular reaction zone, a crossflow can be superimposed on the parallel flow of the salt melt relative to the reaction tubes, so that the individual reaction zone corresponds to a tube bundle reactor as described in EP-A 700714 or in EP-A 700893, resulting in an overall meandering flow path of the heat exchange medium in longitudinal section through the catalyst tube bundle.

In the two-zone method also, the starting reaction gas mixture 1 is advantageously fed to the fixed catalyst bed 1 preheated to the reaction temperature.

Customarily, the catalyst tubes in the two-zone tube bundle reactors are also manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each temperature zone, the fixed catalyst bed 1 occupies at least 60% or at least 75%, or at least 90% of the length of the zone. Any remaining length is optionally occupied by an inert bed. From an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 form the exception. Within the vessel, the catalyst tubes are normally distributed homogeneously, and the distribution is advantageously selected in such a way that the separation of the central internal axes of immediately adjacent catalyst tubes (known as the catalyst tube pitch) is from 35 to 45 mm (cf., for example, EP-B 468290).

Useful heat exchange media for the two-zone method are also in particular fluid heating media. It is particularly advantageous to use melts of salts such as potassium nitrate, potassium nitrite, sodium nitrite and/or sodium nitrate, or of low-melting metals such as sodium, mercury or else alloys of different metals.

In general, in all of the aforementioned flow configurations in the two-zone tube bundle reactor, the flow rate within the two heat exchange medium circuits required is selected in such a way that the temperature of the heat exchange medium from the entry point into the reaction zone to the exit point from the reaction zone (caused by the exothermicity of the reaction) rises by from 0 to 15° C. In other words, the abovementioned ΔT may be from 1 to 10° C., or from 2 to 8° C., or from 3 to 6° C., in accordance with the invention.

According to the invention, the entrance temperature of the heat exchange medium into reaction zone A is normally from 300 to 340° C. According to the invention, the entrance temperature of the heat exchange medium into reaction zone B is normally on the one hand from 305 to 380° C. and is on the other hand, at the same time, at least $\geq 0°$ C., or at least 5° C., above the entrance temperature of the heat exchange medium entering reaction zone A.

At high propene loadings, the entrance temperature of the heat exchange medium in reaction zone B is at least 10° C. above the entrance temperature of the heat exchange medium into reaction zone A. According to the invention, the difference between the entrance temperature into reaction zone A and B may therefore be up to 20° C., up to 25° C., up to 30° C., up to 40° C., up to 45° C. or up to 50° C. However, the abovementioned temperature difference will normally not be more than 50° C. The higher the hourly space velocity of propene on the fixed catalyst bed 1 selected in the process according to the invention, the greater the difference should be between the entrance temperature of the heat exchange medium into reaction zone A and the entrance temperature of the heat exchange medium into reaction zone B.

According to the invention, the entrance temperature of the heat exchange medium into reaction zone B is advantageously from 330 to 370° C. and more advantageously from 340 to 370° C.

It will be appreciated that the two reaction zones A, B in the process according to the invention can also be realized in spatially separated tube bundle reactors. If required, a heat exchanger can also be mounted between the two reaction zones A, B.

It is pointed out once again at this juncture that reaction stage 1 of the process according to the invention can also be carried out using in particular the two-zone tube bundle reactor type described in DE-B 2201528 which includes the possibility of removing a portion of the hotter heat exchange medium of reaction zone B to reaction zone A, in order to optionally effect heating of a cold starting reaction gas mixture or of a cold cycle gas. The tube bundle characteristics within an individual reaction zone can also be configured as described in EP-A 382098.

It has proved advantageous in accordance with the invention to cool the product gas mixture leaving the first reaction stage before entry into the second reaction stage, in order to thus suppress subsequent full combustion of portions of the acrolein formed in the first reaction stage. To this end, an aftercooler is typically arranged between the two reaction stages. In the simplest case, this may be an indirect tube bundle heat exchanger. The product gas mixture is generally conducted through the tubes and a heat exchange medium, whose type may correspond to the heat exchange media recommended for the tube bundle reactors, is conducted around the tubes. Advantageously, the interior of the tube is filled with inert random packings (for example spirals of stainless steel, rings of steatite, spheres of steatite, etc.). These improve the heat exchange and capture any molybdenum trioxide subliming out of the fixed catalyst bed of the first reaction stage before it enters the second reaction stage.

It is advantageous when the aftercooler is manufactured from stainless steel coated with zinc silicate primer.

In general, propene conversion based on single pass in the first reaction stage of the process according to the invention is $\geq 92$ mol % or $\geq 94$ mol %. According to the invention, the resulting selectivity of acrolein formation and also of acrylic acid by-production in the first reaction stage on single pass together will regularly be $\geq 92$ mol % or $\geq 94$ mol %, frequently $\geq 95$ mol % or $\geq 96$ mol % or $\geq 97$ mol %.

The process according to the invention is suitable for hourly space velocities of propene on the fixed catalyst bed 1 of $\geq 80$ l (STP)/l·h, or of $\geq 100$ l (STP)/l·h, or of $\geq 120$ l (STP)/l·h, or of $\geq 140$ l (STP)/l·h, or of $\geq 165$ l (STP)/l·h, or of $\geq 170$ l (STP)/l·h or $\geq 175$ l (STP)/l·h or $\geq 180$ l (STP)/l·h, but also for hourly space velocities of propene on the fixed catalyst bed 1 of $\geq 185$ l (STP)/l·h, or $\geq 190$ l (STP)/l·h or $\geq 200$ l (STP)/l·h or $\geq 210$ l (STP)/l·h, and also for hourly space velocity values of $\geq 220$ l (STP)/l·h or $\geq 230$ l (STP)/l·h or $\geq 240$ l (STP)/l·h or $\geq 250$ l (STP)/l·h.

With increasing hourly space velocity of propene, preference is given to the two-zone method described over the one-zone method described in the first reaction stage.

The up to 10% by volume of constituents of the reaction starting gas mixture 1 other than propene, water, oxygen and nitrogen may, for example, be carbon dioxides such as CO and $CO_2$, acrolein and/or acrylic acid present in the cycle gas or else saturated hydrocarbons, for example propane. With increasing hourly space velocity of propene, it proves advantageous to use propane, for example, as an inert diluent gas.

Normally, the hourly space velocity of propene on the first fixed catalyst bed in the process according to the invention will not exceed 600 l (STP)/l·h. Typically, the hourly space velocities of propene on the fixed catalyst bed 1 in the process according to the invention will be at values of $\leq 300$ l (STP)/l·h, frequently at values of $\leq 250$ l (STP)/l·h.

The working pressure in the first reaction stage of the process according to the invention may either be below atmospheric pressure (for example up to 0.5 bar, the reaction gas mixture is sucked through) or above atmospheric pressure. Typically, the working pressure in the first reaction stage will be at values of from 1 to 5 bar, frequently from 1.5 to 3.5 bar. Normally, the reaction pressure in the first reaction stage will not exceed 100 bar.

A useful source for the molecular oxygen required in the first reaction stage is either air or air depleted of molecular nitrogen.

From an application point of view, the product gas mixture of the first reaction stage is advantageously cooled in the aftercooler already mentioned to a temperature of from 210 to 290° C., frequently from 230 to 280° C. or from 250 to 270° C. The product gas mixture of the first reaction stage can quite feasibly be cooled to temperatures which are below the temperature of the second reaction stage. However, the aftercooling described is in no way obligatory and can generally be dispensed with in particular when the path of the product gas mixture from the first reaction stage into the second reaction stage is kept short. Typically, the process according to the invention is also realized in such a way that the oxygen requirement in the second reaction stage is not already covered by an appropriately high oxygen content of the starting reaction gas mixture 1, but rather that the oxygen required is added in the region between the first and the second reaction stage. This may be effected before, during, after and/or for aftercooling. Useful sources for the molecular oxygen required in the second reaction stage include both pure oxygen and mixtures of oxygen and inert gas, for example air or air depleted of molecular nitrogen (for example $\geq 90\%$ by volume of $O_2$, $\leq 10\%$ by volume of $N_2$). The oxygen source is regularly added compressed to the reaction pressure. It will be appreciated that the oxygen requirement in the second reaction stage of the process according to the invention can already be covered by an appropriately high oxygen requirement in the first reaction stage.

According to the invention, the acrolein content in the starting reaction gas mixture 2 obtained in this way may, for example, be at values of from 5 to 15% by volume, frequently from 6 to 11% by volume or from 7 to 10% by volume (based in each case on the total volume).

According to the invention, the molar $O_2$:acrolein ratio in the starting reaction gas mixture 2 has to be $\geq 0.5$ or $\geq 1$. Typically, this ratio will be at values of $\leq 3$. According to the invention, the molar $O_2$:acrolein ratio in the starting reaction gas mixture 2 will frequently be from 1 to 2 or from 1.5 to 2.0. The steam present in the starting reaction gas mixture 1 and also the steam formed in the first reaction stage are also a constituent of the starting reaction gas mixture 2 in the process according to the invention. Frequently, the process according to the invention will be performed at an acrolein:oxygen:steam:others volume ratio (l (STP)) of 1:(0.9 to 1.3):(2.5 to 3.5):(10 to 12) present in the starting reaction gas mixture 2.

The working pressure in both the second reaction stage and in reaction stage 1 of the process according to the invention may either be below atmospheric pressure (for example up to 0.5 bar) or above atmospheric pressure. According to the invention, the working pressure in the second reaction stage will typically be at values of from 1 to 5 bar, frequently from 1 to 3 bar. Normally, the reaction pressure in the second reaction stage will not exceed 100 bar.

Like the first reaction stage, the second reaction stage of the process according to the invention can be carried out in a simple manner in a tube bundle reactor charged with the fixed catalyst bed 2, as described, for example, in EP-A 700893. The inert beds preceding and/or following the fixed catalyst bed 2 can supplement the charge.

In other words, in the simplest manner, the fixed catalyst bed 2 to be used in accordance with the invention and also any inert beds used are disposed in the metal tubes of a tube bundle reactor and a heating medium (one-zone method), generally a salt melt, is conducted around the metal tubes. Salt melt and reaction gas mixture can be conducted in simple cocurrent or countercurrent. However, the heating medium can also be conducted in a meandering manner around the tube bundle when viewed over the reactor, so that a cocurrent or countercurrent to the flow direction of the reaction gas mixture exists only when viewed over the entire reactor. The flow rate of the heating medium (heat exchange medium) is typically such that the temperature rise (caused by the exothermicity of the reaction) of the heat exchange medium from the entry point into the reactor to the exit point from the reactor is from $\geq 0$ to $10°$ C., frequently from $\geq 2$ to $8°$ C., often from $\geq 3$ to $6°$ C. The entrance temperature of the heat exchange medium into the tube bundle reactor is generally from 230 to $300°$ C., frequently from 245 to $285°$ C. or from 255 to $275°$ C. Useful heat exchange media are the same fluid heating media as have already been described for the first reaction stage.

Advantageously, the reaction gas mixture 2 is fed to the fixed catalyst bed 2 preheated to the reaction temperature. For the dimensioning of the catalyst tubes, the catalyst tube material, the number of catalyst tubes and their charging with fixed catalyst bed 2/inert bed, the same applies as was said for the tube bundle reactor of the first reaction stage.

In general, a one-zone method of the first reaction stage is combined with a one-zone method of the second reaction stage, and the relative flow of reaction gas mixture and heating medium selected in both stages is identical.

It will be appreciated that the second reaction stage of the process according to the invention can also be realized in a corresponding manner to the first reaction stage as two spatially successive reaction zones C, D, and the temperature of reaction zone C (this always means the temperature of the entering salt bath or heat carrier in general) is advantageously from 230 to $270°$ C. and the temperature of reaction zone D is from 250 to $300°$ C. and, at the same time, at least $\geq 0°$ C., or at least $\geq 5°$ C., above the temperature of the reaction zone C.

Reaction zone C preferably extends to an acrolein conversion of from 65 to 80 mol %. The temperature of reaction zone C is also advantageously from 245 to $260°$ C. At higher acrolein loadings, the temperature of reaction zone D is preferably from 5 to $10°$ C. above the temperature of reaction zone C and is advantageously from 260 to $285°$ C. For the two-zone method of the second reaction stage stage too, the same applies with regard to the reactor for the dimensioning of the catalyst tubes, the catalyst tube material, the number of catalyst tubes and their charging with fixed catalyst bed 2/inert bed as was said for the two-zone tube bundle reactor of the first reaction stage.

The higher the hourly space velocity of acrolein on the fixed catalyst bed 2 selected in the process according to the invention, the greater the preference given to the two-zone method over the one-zone method and the greater should be the difference selected between the temperature of reaction zone C and the temperature of reaction zone D. However, the abovementioned temperature difference will not normally be more than $40°$ C. In other words, the difference between the temperature of reaction zone C and the temperature of reaction zone D may be up to $15°$ C., up to $25°$ C., up to $30°$ C., up to $35°$ C. or up to $40°$ C., in accordance with the invention.

Generally, in the process according to the invention, the acrolein conversion based on single pass in the second reaction stage of the process according to the invention may be $\geq 92$ mol %, or $\geq 94$ mol %, or $\geq 96$ mol %, or $\geq 98$ mol % and frequently even $\geq 99$ mol %. The selectivity of acrylic acid formation, based on acrolein converted, may regularly be $\geq 92$ mol %, or $\geq 94$ mol %, frequently $\geq 95$ mol % or $\geq 96$ mol %, or $\geq 97$ mol %.

The process according to the invention is suitable for hourly space velocities of acrolein on the fixed catalyst bed 2 of $\geq 80$ l (STP)/l·h, or of $\geq 100$ l (STP)/l·h, or of $\geq 120$ l (STP)/l·h, or of $\geq 140$ l (STP)/l·h or $\geq 150$ l (STP)/l·h, or of $\geq 160$ l (STP)/l·h or $\geq 170$ l (STP)/l·h, or $\geq 175$ l (STP)/l·h, or $\geq 180$ l (STP)/l·h, but also at hourly space velocities of acrolein on the fixed catalyst bed 2 of $\geq 185$ l (STP)/l·h, or of $\geq 190$ l (STP)/l·h, or $\geq 200$ l (STP)l/l·h, or $\geq 210$ l (STP)/l·h, and also at hourly space velocity values of $\geq 220$ l (STP)/l·h, or $\geq 230$ l (STP)/l·h or $\geq 240$ l (STP)/l·h, or $\geq 250$ l (STP)/l·h.

With preference in accordance with the invention, no secondary gas consisting only of inert gas is metered in between the first and the second reaction stage.

The hourly space velocity of acrolein of the second fixed catalyst bed in the process according to the invention will normally not exceed the value of 600 l (STP)/l·h. Typically, the hourly space velocities of acrolein on the fixed catalyst bed 2 in the process according to the invention without significant loss of conversion and selectivity is at values of ≦300 l (STP)/l·h, frequently at values of ≦250 l (STP)/l·h.

In general, the hourly space velocity of acrolelin on the second fixed catalyst bed will be about 10 l (STP)/l·h, frequently about 20 or 25 l (STP)/l·h below the hourly space velocity of propene on the first catalyst bed. This can primarily be attributed to neither conversion nor selectivity for acrolein in the first reaction stage generally reaching 100%. The oxygen requirement in the second reaction stage is also typically covered by air as the secondary gas. With increasing hourly space velocity of acrolein, preference is given in the second reaction stage to the two-zone method described over the one-zone method detailed.

Remarkably, the selectivity of acrylic acid formation assessed over both reaction stages of the process according to the invention, based on converted propene, even at the highest hourly space velocities of propene and acrolein is generally at values of ≧83 mol %, frequently at ≧85 mol % or ≧88 mol %, often at ≧90 mol % or ≧93 mol %.

In an advantageous manner from an application point of view, the second reaction stage of the process according to the invention is carried out in a two-zone tube bundle reactor. A preferred variant of a two-zone tube bundle reactor which can be used for the second stage in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903582 are also suitable for carrying out the second reaction stage of the process according to the invention.

In other words, in a simple manner, the fixed catalyst bed 2 (optionally including the inert beds) to be used in accordance with the invention is disposed in the metal tubes of a tube bundle reactor and two substantially spatially separate heating media, generally salt melts, are conducted around the metal tubes. The tube section over which the particular salt bath extends represents a reaction zone in accordance with the invention.

In other words, in a simple manner, a salt bath C, for example, flows around those sections of the tubes (reaction zone C) in which acrolein is oxidatively converted (on single pass) until a conversion value in the range from 55 to 85 mol % is achieved and a salt bath D flows around the section of the tubes (reaction zone D) in which the acrolein is subsequently oxidatively converted (on single pass) until a conversion value of at least 90 mol % is achieved (if required, the reaction zones C,D to be used in accordance with the invention may be followed by further reaction zones which are maintained at individual temperatures).

Advantageously from an application point of view, the reaction zone 2 of the process according to the invention includes no further reaction zones. In other words, salt bath D advantageously flows around the section of the tubes in which the acrolein is subsequently oxidatively converted (on single pass) up to a conversion value of ≧92 mol %, or ≧94 mol %, or ≧96 mol %, or ≧98 mol %, and frequently even ≧99 mol % or more.

Typically, the beginning of reaction zone D is beyond the heating point maximum of reaction zone C The temperature of the heating point maximum of reaction zone D is normally below the heating point maximum temperature of reaction zone C.

According to the invention, the two salt baths C, D can be conducted in cocurrent or in countercurrent through the space surrounding the reaction tubes relative to the flow direction of the reaction gas mixture flowing through the reaction tubes. It will be appreciated that cocurrent flow can also be applied in reaction zone C and countercurrent flow in reaction zone D (or vice versa) in accordance with the invention.

It will be appreciated that in all the abovementioned configurations within a particular reaction zone, a crossflow can be superimposed on the parallel flow of the salt melt relative to the reaction tubes, so that the individual reaction zone corresponds to a tube bundle reactor as described in EP-A 700714 or in EP-A 700893, resulting in an overall meandering flow path of the heat exchange medium in longitudinal section through the catalyst tube bundle.

Typically, the catalyst tubes in the abovementioned two-zone tube bundle reactors (as in the tube bundle reactors of the one-zone method) are manufactured from ferritic steel and typically have a wall thickness of from 1 to 3 mm. Their internal diameter is generally from 20 to 30 mm, frequently from 22 to 26 mm. Their length is advantageously from 3 to 4 m, preferably 3.5 m. In each temperature zone, the fixed catalyst bed 2 occupies at least 60%, or at least 75%, or at least 90%, of the length of the zone. Any remaining length is optionally occupied by an inert bed. From an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 generally form the exception. Within the vessel, the catalyst tubes are normally homogeneously distributed, and the distribution is advantageously selected in such a way that the separation of central internal axes of immediately adjacent catalyst tubes (known as the catalyst tube pitch) is from 35 to 45 mm (cf. EP-B 468290).

Useful heat exchange media are in particular fluid heating media. It is particularly advantageous to use melts of salts such as potassium nitrate, potassium nitrite, sodium nitrite and/or sodium nitrate, or of low-melting metals such as sodium, mercury or else alloys of different metals.

In general, all of the abovementioned flow configurations in the two-zone tube bundle reactors, the flow rate within the two heat exchange medium circuits required is selected in such a way that the temperature of the heat exchange medium from the entry point into the reaction zone to the exit point from the reaction zone rises by from 0 to 15° C. In other words, the aforementioned ΔT may be from 1 to 10° C., or from 2 to 8° C. or from 3 to 6° C., in accordance with the invention.

The entrance temperature of the heat exchange medium into reaction zone C in the second reaction stage of a two-zone method according to the invention is normally from 230 to 270° C. According to the invention, the entrance temperature of the heat exchange medium into reaction zone D is normally on the one hand from 250 to 300° C. and on the other hand, at the same time, at least ≧0° C., or at least ≧5° C., above the entrance temperature of the heat exchange medium entering reaction zone C.

At high acrolein loadings, the entrance temperature of the heat exchange medium into reaction zone D is preferably from 5 to 10° C. above the entrance temperature of the heat exchange medium entering reaction zone C. According to the invention, the difference between the extreme temperatures into reaction zone C and D may also be up to 15° C., up to 25° C., up to 30° C., up to 35° C. or up to 40° C. However, the abovementioned temperature will normally not be more than 50° C. The higher the hourly space velocity of acrolein on the catalyst bed 2 selected in the process according to the invention, the greater should be the difference between the entrance temperature of the heat exchange medium into reaction zone C and the entrance temperature of the heat exchange medium into reaction zone D. The entrance temperature of the heat exchange medium into reaction zone C is preferably from 245 to 260° C. and the entrance temperature into reaction zone D from 260 to 285° C.

It will be appreciated that the two reaction zones C, D in the process according to the invention can also be realized in spatially separate tube bundle reactors. If required, a heat exchanger can also be mounted between the two reaction zones C, D.

It is pointed out once again at this juncture that the second reaction stage of the process according to the invention can be carried out using in particular the two-zone tube bundle reactor type described in DE-B 2201528 which includes the possibility of removing a portion of the hotter heat exchange medium of reaction zone D to reaction zone C, in order to effect heating of a too-cold starting reaction gas mixture 2 or of a cold cycle gas. The tube bundle characteristics within an individual reaction zone can also be configured as described in EP-A 382 098.

It will be appreciated that two one-zone tube bundle reactors for the two reaction stages can also be combined in the process according to the invention to a single two-zone reactor to be operated in another manner, as described, for example, in DE-C 2830765, EP-A 911313 and EP-A 383 224. In this case, the first reaction stage is realized in the first reaction zone and the second reaction stage in the second reaction zone of the two-zone tube bundle reactor.

In complete correspondence, one one-zone tube bundle reactor and one two-zone tube bundle reactor or two two-zone tube bundle reactors can also each be combined to a single tube bundle reactor which then has three or four temperature zones and is described, for example, in WO 01/36364.

In this case, for example, the first reaction stage can be carried out in the first reaction zone and the second reaction stage in the two subsequent reaction zones of the three-zone tube bundle reactor. Alternatively, for example, the first reaction stage can be carried out in the first two reaction zones and the second reaction stage in the two subsequent reaction zones of the four-zone tube bundle reactor, etc. The salt bath temperature of the individual temperature zones may be configured as described in the case of spatially separate tube bundle reactors. Normally, an inert bed is disposed in these cases between fixed catalyst bed 1 and fixed catalyst bed 2. However, such an intermediate inert bad can also be dispensed with. The length of the reaction tubes in the cases of combination in many cases corresponds to the sum of the lengths of the uncombined tube bundle reactors. It will be appreciated that the process according to the invention can also be performed in a similar manner to the methods described in the documents EP-A 990636 and EP-A 1106598.

It is surprising that the yield $Y^{AA}$ of acrylic acid in the process according to the invention is increased relative to the nearest prior art processes, without requiring an increased compressor output or the use of material of value as an inert diluent gas for this increase, or accompanying increased by-production of acetic acid.

It will be appreciated that the process according to the invention does not provide pure acrylic acid, but rather a product gas mixture from whose secondary components the acrylic acid is removed in a manner known per se (for example, basic separation by fractional condensation or by absorption in an aqueous or in an organic solvent and also subsequent rectificative and/or crystallizative removal from condensate or absorbate). Unconverted acrolein, propene and also inert diluent gas used and/or formed in the course of the reaction can be recycled into the first reaction stage.

Useful crude propene for the process according to the invention is, for example, propene of polymer grade quality and of chemical grade quality, as described, for example, in DE-A 10254279.

Unless stated otherwise, conversion and selectivity in this document are defined as follows:

Conversion $C$ of reactant(%) =
$$\frac{\text{Number of moles of reactants converted}}{\text{Number of moles of reactants used}} \times 100;$$

Selectivity $S$ of product formation(%) =
$$\frac{\text{Number of moles of reactants converted to product}}{\text{Number of moles of reactants converted}} \times 100;$$

Yield Y of product (%)=(S·C)/100.

EXAMPLES AND COMPARATIVE EXAMPLES

I. Single Catalyst Tube Experiment

A) General Experimental Construction Reactor for the First Reaction Stage

The reactor consisted of a jacketed cylinder of stainless steel (cylindrical guide tube, surrounded by a cylindrical external vessel). The wall thicknesses were always 2 to 5 mm.

The internal diameter of the external cylinder was 91 mm. The internal diameter of the guide tube was approx. 60 mm.

At the top and the bottom, the jacketed cylinder was enclosed by a lid and a bottom respectively.

The catalyst tube (total length 400 cm, internal diameter 26 mm, external diameter 30 mm, wall thickness 2 mm, stainless steel) was accommodated in the cylindrical vessel in such a way that it just protruded at the upper and lower ends (sealed) through the top and bottom. The heat exchange medium (salt melt, consisting of 53% by weight of potassium nitrate, 40% by weight of sodium nitrite and 7% by weight of sodium nitrate) was enclosed in the cylindrical vessel. In order to ensure very uniform thermal boundary conditions at the external wall of the catalyst tube over the entire catalyst tube length disposed in the cylindrical vessel (400 cm), the heat exchange medium was circulated by pumping by means of a propeller pump.

An electrical heater mounted on the jacket allowed the temperature of the heat exchange medium to be controlled to the desired level. Otherwise, there was air cooling.

Reactor charge: Viewed over the first stage reactor, salt melt and the starting reaction gas mixture 1 were conducted in cocurrent. The starting reaction gas mixture 1 entered the first stage reactor from below. It was conducted into the reaction tube in each case at a temperature of 165° C.

The salt melt entered the cylindrical guide tube from below at a temperature $T^{in}$=320° C. and exited from the top of cylindrical guide tube at a temperature $T^{out}$ which was up to 2° C. above $T^{in}$.

Catalyst tube charge: (from bottom to top) Section A: length 90 cm

Preliminary bed of steatite spheres of diameter 4–5 mm.
  Section B: length 100 cm
    Catalyst charge of a homogeneous mixture of 30% by weight of steatite rings of geometry 5 mm×3 mm×2 mm (external diameter×length×internal diameter) and 70% by weight of unsupported catalyst from section C.
  Section C: length 200 cm
    Catalyst charge of annular (5 mm×3 mm×2 mm=external diameter×length×internal diameter) unsupported catalyst according to example 1 of DE-A 10046957 (stoichiometry: $[Bi_2W_2O_9 \times 2WO_3]_{0.5}[Mo_{12}Co_{5.5}Fe_{2.94}Si_{1.59}K_{0.08}O_x]_1$)
  Section D: length 10 cm
    Subsequent bed of steatite rings of geometry 7 mm×3 mm×4 mm (external diameter×length×internal diameter)

Intermediate Cooling and Optionally Intermediate Oxygen Feeding (Air as Secondary Gas)

The product gas mixture leaving the first fixed catalyst bed reactor was conducted for the purposes of intermediate cooling (indirectly by means of air) through a connecting tube (length 40 cm, internal diameter 26 mm, external diameter 30 mm, wall thickness 2 mm, stainless steel, wound round with 1 cm insulating material) which was mounted centered at a length of 20 cm, charged with an inert bed of steatite rings of geometry 7 mm×3 mm×4 mm (external diameter×length×internal diameter) and flanged directly onto the first stage catalyst tube.

In all cases, the product gas mixture entered the connecting tube at a temperature of more than 320° C. and leaves it at a temperature above 200° C. and below 270° C.

Depending on the requirements, air compressed to the pressure of the product gas mixture can be metered into the cold product gas mixture at the end of the connecting tube. The resulting gas mixture was conducted directly into the second stage catalyst tube, to which the abovementioned connecting tube was likewise flanged at its other end.

Reactor for the Second Reaction Stage

A catalyst tube fixed bed reactor was used which was identical in design to that for the first reaction stage. Salt melt and reaction gas mixture were conducted in cocurrent as viewed over the reactor. The salt melt entered at the bottom, and the starting reaction gas mixture 2 likewise. The entrance temperature $T^{in}$ of the salt melt was set in such a way that an acrolein conversion of 99.3±0.1 mol % on single pass resulted in all cases. $T^{out}$ of the salt melt was at 2° C. above $T^{in}$.

The catalyst tube charge (from bottom to top) was:
Section A: length 70 cm
Preliminary bed of steatite rings of geometry 7 mm×3 mm×4 mm (external diameter×length×internal diameter)
Section B: length 100 cm
Catalyst charge with a homogeneous mixture of 45% by weight of steatite rings of geometry 7 mm×3 mm×4 mm (external diameter×length×internal diameter) and 70% by weight of coated catalyst from section C.
Section C: length 200 cm
Catalyst charge of annular (7 mm×3 mm×4 mm=external diameter×length×internal diameter) coated catalyst according to example 5 of DE A 10046928 (stoichiometry: $Mo_{12}V_3W_{1.2}Cu_{2.4}O_x$).
Section D: length 30 cm
Subsequent bed of steatite spheres of diameter 4–5 mm.

Removal of Acrylic Acid from the Product Gas Mixture of the Second Reaction Stage The product gas mixture coming from the second reaction stage was subjected to direct cooling by means of water which contained 350 ppm by weight of hydroquinone (HQ) as a polymerization inhibitor (temperature=4° C.) in a Venturi separator (similar in construction to the Venturi tubes and accelerate the gas mixture at the narrowest point of the Venturi tube, at the same time spray in the cooling water and intensively mix in the turbulent flow field resulting in high pressure drops; downstream separators separate the liquid phase) and the resulting mixture is fed to a liquid phase separator. The separated aqueous phase was recycled via a heat exchanger into the Venturi separator (360 l/h). Excess aqueous phase was continuously removed.

The product gas mixture cooled to a temperature of 30° C. was conducted from below into an absorption column which contained 11 bubble-cap trays in equidistant arrangement (tray separation: 54 mm; tray diameter: 12 mm) and subjected to the countercurrent of 0.55 kg/h of HQ-stabilized water as an absorbent (introduced at a temperature of 2° C. at the top of the column). 1.7 kg of approx. 40% aqueous acrylic acid were withdrawn per hour from the bottom of the column. Depending on the requirements, the residual gas leaving the absorption column at the top was fed to incineration and/or used as cycle gas to form the starting reaction gas mixture 1 (recycled via a compressor to the reactor of the first reaction stage).

B) Results Achieved as a Function of the Composition of the Starting Reaction Gas Mixture 1

1. Inventive Example

The composition of the starting reaction gas mixture 1 was:
7.1% by volume of propene,
10.4% by volume of water,
0.5% by volume of constituents other than propene, water, oxygen and nitrogen, molar ratio of molecular oxygen present to propene present=1.73, and a remainder of molecular nitrogen.

The hourly space velocity of propene on the fixed catalyst bed 1 was 150 l (STP)/l·h. The oxygen source was air. No air was added as a secondary gas. The starting reaction gas mixture contained 3.6 mol of cycle gas per mole of propene. The yield $Y^{AA}$ (in the product gas mixture leaving the second reaction phase) was 89.3%. The acetic acid by-product yield detected at the same point was 1.44%.

Propene conversion (first reaction stage exit)=97.8%.
Selectivity of acrolein formation and acrylic acid by-production together (first reaction stage exit)=97.2%.
Acrolein conversion (second reaction stage exit)=99.3%.
$S^{AA}$ (second reaction stage exit)=94.8%.

2. Comparative Example

The composition of the starting reaction gas mixture 1 was:
5.3% by volume of propene,
2.4% by volume of water,
0.66% by volume of constituents other than propene, water, oxygen and nitrogen, molar ratio of molecular oxygen present to propene present=1.73, and a remainder of molecular nitrogen.

The hourly space velocity of propene on the fixed catalyst bed 1 was 150 l (STP)/l·h. The oxygen source was air. No air was added as a secondary gas. The starting reaction gas mixture contained 8 mol of cycle gas per mole of propene.

The yield $Y^{AA}$ (in the product gas mixture leaving the second reaction stage) was 88.8%. The acetic acid by-product yield detected at the same point was 1.45%.

Propene conversion (first reaction stage exit)=97.5%.

Selectivity of acrolein formation and acrylic acid by-production together (first reaction stage exit)=97.0%.

Acrolein conversion (second reaction stage exit)=99.3%.

$S^{AA}$ (second reaction stage exit)=94.6%.

3. Inventive Example

The composition of the starting reaction gas mixture 1 was:

7.1% by volume of propene, 10.2% by volume of water, 0.5% by volume of constituents other than propene, water, oxygen and nitrogen, molar ratio of molecular oxygen present to propene present=1.73, and a remainder of molecular nitrogen.

In contrast to the example and comparative example, the dilution in section B of the second reaction stage was only 30% by weight.

The hourly space velocity of propene on the fixed catalyst bed 1 was 130 l (STP)/l·h. The oxygen source was air. No air was added as a secondary gas. The starting reaction gas mixture contained 4 mol of cycle gas per mole of propene.

The yield $Y^{AA}$ (in the product gas mixture leaving the second reaction stage) was 89.5%.

Propene conversion (first reaction stage exit)=97.6%.

Selectivity of acrolein formation and acrylic acid by-production together (first reaction stage exit)=97.3%.

Acrolein conversion (second reaction stage exit)=99.3%.

$S^{AA}$ (second reaction stage exit)=94.7%.

4. Inventive Example

The procedure of "3" was repeated. However, the molar ratio of molecular oxygen present in the starting reaction gas mixture 1 to propene contained therein was 1.53 instead of 1.73. In addition, air compressed to reaction pressure at a temperature of 160° C. was added as secondary gas to the reaction gas mixture between the exit and intermediate cooling and entry into the second reaction stage. The molar amount of secondary air added was 2.78 times the molar amount of propene present in the starting reaction gas mixture 1.

The yield $Y^{AA}$ (in the product gas mixture leaving the second reaction stage) was 89.1%.

Propene conversion (first reaction stage exit)=97.7%.

Selectivity of acrolein formation and of acrylic acid by-production together (first reaction stage exit)=96.9%.

Acrolein conversion (second reaction stage exit)=99.4%.

$S^{AA}$ (second reaction stage exit)=94.7%.

As described, the above examples and the comparative example can also be carried out in accordance with the invention when the length of section C in the second reaction stage is lengthened to 2.25 m or shortened to 1.50 m in a reaction tube lengthened or shortened in a corresponding manner. It is possible to vary, for example, Tin of the first reaction stage within the range from 315 to 325° C. and $T^{in}$ of the second reaction stage within the range from 270° C. to 280° C. It is also possible to vary the steam content of the starting reaction gas mixture 1, for example, between 4% by volume and 12% by volume.

II. Multiple Catalyst Tube Experiment

A) Process for heterogeneously catalyzed gas phase partial oxidation of propylene to acrylic acid in two stages into two one-zone multiple-ctalyst-tube fixed bed reactors connected in series

1. Description of the General Process Conditions in the First Stage

| | |
|---|---|
| Heat exchange medium: | salt melt consisting of 60% by weight of potassium nitrate and 40% by weight of sodium nitrite. |
| Material of the catalyst tubes: | ferritic steel. |
| Dimensions of the catalyst tubes: | length 3200 mm; internal diameter 25 mm; external diameter 30 mm; (wall thickness: 2.5 mm). |
| Number of catalyst tubes in the tube bundle: | 25500. |
| Reactor: | cylindrical vessel of diameter 6800 mm; tube bundle arranged in a ring with a free central space. |

Diameter of the central free space: 1 000 mm. Separation of the outermost catalyst tubes to the vessel wall: 150 mm. Homogeneous catalyst tube distribution in the tube bundle (6 equidistant adjacent tubes per catalyst tube).

Catalyst tube pitch: 38 mm.

The catalyst tubes are secured at their ends with sealing in catalyst tube plates of thickness 125 mm and their openings each open at the upper and lower end into a hood joined to the vessel.

Feed of the heat exchange medium to the tube bundle:

The tube bundle is divided by three deflecting plates (thickness in each case 10 mm) disposed in succession between the catalyst tube plates in the longitudinal direction thereof into four equidistant (each 730 mm) longitudinal sections (zones).

The uppermost and the lowermost deflecting plates have annular geometry, and the internal annular diameter is 1 000 mm and the external annular diameter extends to and is sealed to the vessel wall. The catalyst tubes are secured to the deflecting plates without sealing. Rather, a gap having a gap width of <0.5 mm is left so that the transverse flow rate of the salt melt within a zone is substantially constant.

The middle deflecting plate is circular and extends up to the outermost catalyst tubes of the tube bundle.

The circulation of the salt melt is achieved by two salt pumps, each of which supplies half of the tube bundle length.

The pumps force the salt melt into an annular channel which is disposed at the bottom around the reactor jacket and distributes the salt melt over the vessel circumference. The salt melt passes through the window disposed in the reactor jacket into the lowermost longitudinal section of the tube bundle. The salt melt then flows, under the control of the deflecting plates, in the sequence from the outside inward, from the inside outward, from the outside inward, from the inside outward, substantially in a meandering manner, viewed over the vessel, from bottom to top. The salt melt collects in an upper annular channel disposed around the reactor jacket through the window disposed around the vessel circumference in the uppermost longitudinal section and, after cooling to the original entrance temperature, is forced back into the lower annular channel by the pumps.

| | |
|---|---|
| Reactor charge: | salt melt and reaction gas mixture are conducted in countercurrent viewed over the reactor. The salt melt enters at the bottom, the reactor mixture at the top. The entrance temperature of the salt melt at the start is approx. 337° C. The exit temperature of the salt melt is approx. 339° C. The pump output is approx. 6200 m³ of salt melt/h. The starting reaction gas mixture is fed to the reactor at a temperature of 300° C. |
| Loading with starting reaction gas mixture: | approx. 69000 Nm³/h. |
| Catalyst tube charge (from top to bottom): | Zone A: 50 cm Preliminary bed of steatite rings of geometry 7 mm × 7 mm × 4 mm (external diameter × length × internal diameter) Zone B: 100 cm Catalyst charge of a homogeneous mixture of 30% by weight of steatite rings of geometry 5 mm × 3 mm × 2 mm (external diameter × length × internal diameter) and 70% by weight of unsupported catalyst from Zone C). Zone C: 170 cm Catalyst charge of annular (5 mm × 3 mm × 2 mm = external diameter × length × internal diameter) unsupported catalyst according to example 1 of DE-A 10046957. |

2. Description of the Intermediate Cooling

For the purpose of intermediate cooling, the product gas mixture leaving the first reaction stage is conducted through a one-zone tube bundle heat exchanger cooled with a salt melt of 60% by weight of potassium nitrate and 40% by weight of sodium nitrite and made of ferritic steel, which is flanged directly onto the reactor. The separation of the lower tube plate of the reactor to the upper tube plate of the cooler is 10 cm. The salt melt and the product gas mixture are conducted in countercurrent viewed over the heat exchanger. The salt bath itself flows in the same way as in the one-zone multiple-catalyst-tube fixed bed reactor, in a meandering manner around the cooling tubes through which the product gas mixture is passed. The length of the cooling tubes is 1.65 m, their internal diameter is 2.6 cm and their wall thickness is 2.5 mm. The number of cooling tubes is 8 000. The diameter of the heat exchanger is 7.2 m.

They are distributed in uniform tube pitch uniformly over the cross section.

Stainless steel spirals are introduced into the entrance of the cooling tubes (in the flow direction), the cross section of said spirals substantially corresponding to that of the cooling tubes. They serve to improve the heat transfer.

The product gas mixture leaves the intermediate cooler at a temperature of about 250° C. Subsequently, compressed air having a temperature of 140° C. is mixed with it if required.

The resulting charging gas mixture is fed to the second stage of the one-zone multiple-catalyst-tube fixed bed reactor at a temperature of 220° C.–250° C.

3. Description of the General Process Conditions in the Second Stage

A one-zone multiple-catalyst-tube fixed bed reactor identical in design to that of the first stage is used.

Salt melt and reaction gas mixture are conducted in countercurrent viewed over the reactor. The salt melt enters from below, the reaction mixture from above.

The entrance temperature of the salt melt at the start is approx. 265° C. The exit temperature of the salt melt is approx. 267° C. The pump output is 6 200 m³ of salt melt/h.

The loading with charging gas mixture is about 75 000 m³ (STP)/h.

The catalyst tube charge (from top to bottom) is:
Zone A:
  20 cm preliminary bed of steatite rings of geometry 7 mm × 7 mm × 4 mm (external diameter × length × internal diameter).
Zone B:
  100 cm catalyst charge of a homogeneous mixture of 30% by weight of steatite rings of geometry 7 mm × 3 mm × 4 mm (external diameter × length × internal diameter) and 70% by weight of coated catalyst of Zone C.
Zone C:
  200 cm catalyst charge of annular (approx. 7 mm × 3 mm × 4 mm) coated catalyst according to preparation example 5 of DE A 10046928.

B) Instead of the one-zone multiple-catalyst-tube fixed bed reactors, the two-zone multiple-catalyst-tube fixed bed reactors according to DE-A 19910506 and DE-A 19910508 and the process conditions specified in these documents can also be used.

C) Both in embodiment II. A) and in embodiment II. B), the first stage catalyst used may also be the catalyst of example 3 of DE-A 10046957, and the second stage catalyst used are catalysts according to DE-A 19815281. The volume-specific activity profile is retained.

In the embodiments II. A, B, C, the reactor is charged with a starting reaction gas mixture of the following composition:
6.0% by volume of propene
60% by volume of air and
34% by volume of $H_2O$.

Downstream of the intermediate cooler, it is possible either to add air (so that the molar ratio of oxygen to acrolein in the charging gas mixture of the second stage is 1.6) or to dispense with air addition. In both cases, the yield $Y^{AA}$ of acrylic acid, based on converted propene, is $\geq 89$ mol %.

Alternatively, for both process variants (with or without secondary air addition), the starting reaction gas mixture used may also be a reaction gas mixture of the composition of example 1 of EP-A 990 636, or of example 2 of EP-A 990 636, or of example 3 of EP-A 1 106 598, or of example 26 of EP-A 1 106 598, or of example 53 of EP-A 1 106 598.

We claim:
1. A process for partially oxidizing propene to acrylic acid in the gas phase under heterogeneous catalysis by initially conducting a starting reaction gas mixture 1 comprising propene, molecular oxygen and at least one inert gas and containing the molecular oxygen and the propene in a molar $O_2:C_3H_6$ ratio of $\geq 1$ in a first reaction stage at elevated temperature over a first fixed catalyst bed
  whose shaped catalyst bodies are annular,
  whose active composition is at least one multimetal oxide I of the general formula

$$Mo_{12}X^1{}_a X^2{}_b X^3{}_c X^4{}_d X^5{}_e O_n \qquad (I),$$

where the variables are defined as follows:
  $X^1$=at least one element from the group comprising Bi, Co and Ni,
  $X^2$=at least one of the two elements W and Nb,
  $X^3$=at least one of the two elements Fe and Cr,
  $X^4$=at least one element from the group comprising K, Cs and Sr,
  $X^5$=at least one element from the group comprising Si, Al and Zr,
  a=from 5 to 10,
  b=from 0 to 4,
  c=from 2 to 5,
  d=from 0.02 to 0.15,
  e=from 0.5 to 4, and
  n=a number which is determined by the valency and frequency of the elements in I other than oxygen,
  whose volume-specific activity in the flow direction of the reaction gas mixture over the first fixed catalyst bed is either constant or increases at least once, and
  whose active composition does not change over the first fixed catalyst bed,
in such a way that the propene conversion on single pass is $\geq 90$ mol% and the accompanying selectivity of acrolein formation and also of acrylic acid by-production together are $\geq 90$ mol %, the temperature of the product gas mixture leaving the first reaction stage is optionally reduced by direct cooling, or by indirect cooling, or by direct and indirect cooling, secondary gas is optionally added to the product gas mixture in the form of molecular oxygen, or inert gas, or molecular oxygen and inert gas, and the product gas mixture is afterwards conducted as the starting reaction gas mixture 2 comprising acrolein, molecular oxygen and at least one inert gas and containing the molecular oxygen and acrolein in a molar $O_2:C_3H_4O$ ratio of $\geq 0.5$ in a second reaction stage at elevated temperature over a second fixed catalyst bed,
  whose shaped catalyst bodies are annular,
  whose active composition comprises at least one multimetal oxide II of the general formula

$$Mo_{12}V_f X^6_g X^7_h O_m \qquad (II)$$

where the variables are defined as follows:
  $X^6$=at least one of the two elements W and Nb,
  $X^7$=at least one of the elements from the group comprising Sb, Cu, Ni and Fe,
  f=from 1 to 5,
  g=from 1 to 2,
  h=from 1 to 4, and
  m=a number which is determined by the valency and frequency of the elements in II other than oxygen,
  whose volume-specific activity in the flow direction of the reaction gas mixture over the second fixed catalyst bed increases at least once, and
  whose active composition does not change over the second fixed catalyst bed,
in such a way that the acrolein conversion on single pass is $\geq 90$ mol % and the selectivity $S^{AA}$ of the acrylic acid formation assessed over both reaction stages, based on converted propene, is $\geq 80$ mol %,
  wherein the starting gas reaction mixture 1 comprises
  from 6 to 15% by volume of propene,
  from 4 to 20% by volume of water,
  from 0 to 10% by volume of constituents other than propene, water, oxygen and nitrogen,
sufficient molecular oxygen that the molar ratio of molecular oxygen present to molecular propene present is from 1.5 to 2.5, and the remainder up to 100% by volume of the total amount of molecular nitrogen.

2. A process as claimed in claim 1, wherein the starting reaction gas mixture 1 comprises from 6 to 15% by volume of water.

3. A process as claimed in claim 1, wherein the starting reaction gas mixture 1 comprises from 0 to 5% by volume of constituents other than propene, water, oxygen and nitrogen.

4. A process as claimed in claim 1, wherein the starting reaction gas mixture 1 comprises
  from 7 to 11% by volume of propene,
  from 6 to 12% by volume of water,
  from 0 to 5% by volume of constituents other than propene, water, oxygen and nitrogen,
  sufficient molecular oxygen that the molar ratio of molecular oxygen present to molecular propene present is from 1.6 to 2.2, and a remainder of molecular nitrogen up to 100% by volume of the total amount.

5. A process as claimed in claim 1, wherein
  $X^1$=at least one of the two elements Bi and Co,
  $X^2$=at one two elements W and Nb,
  $X^3$=Fe,
  $X^4$=at least one of the two elements K and Cs,
  $X^5$=at least one of the two elements Si and Zr,
  a=from 6 to 8,
  b=from 0 to 2.5,
  c=from 2 to 4,
  d=from 0.04 to 0.1, and
  e=from 1 to 3.

6. A process as claimed in claim 1, wherein
  $X^6$=at least one of the two elements W and Nb,
  $X^7$=at least one of the two elements Cu and Sb,
  f=from 2 to 4,
  g=from 1 to 2, and
  h=from 1 to 3.

7. A process as claimed in claim 1, wherein the shaped catalyst bodies of the first fixed catalyst bed are annular unsupported catalysts.

8. A process as claimed in claim 1, wherein the shaped catalyst bodies of the second fixed catalyst bed are annular coated catalysts.

9. A process as claimed in claim 1, wherein the annular geometry of the shaped catalyst bodies in both fixed catalyst beds has the following dimensions:
  from 2 to 11 mm for the external annular diameter,
  from 2 to 11 mm for the annular length and
  from 1 to 5 mm for the wall thickness of the ring.

10. A process as claimed in claim 1, wherein the shaped catalyst bodies of the second fixed catalyst bed are annular coated catalysts whose support rings have a length of from 2 to 10 mm, an external diameter of from 2 to 10 mm and a wall thickness of from 1 to 4 mm.

11. A process as claimed in claim 1, wherein the shaped catalyst bodies of the first fixed catalyst bed are annular unsupported catalysts whose internal diameter is from 0.1 to 0.7 times the external diameter and whose length is from 0.5 to 2 times the external diameter.

12. A process as claimed in claim 1, wherein the shaped catalyst bodies of the second fixed catalyst bed are annular coated catalysts whose active composition content is from 10 to 30% by weight.

13. A process as claimed in claim 1, wherein the first fixed catalyst bed in the flow direction of the reaction gas mixture is structured as follows:
  to a length of from 10 to 60% of the total length of the first fixed catalyst bed, a homogeneous mixture of shaped catalyst bodies and shaped diluent bodies and then, up to the end of the length of the first fixed catalyst bed, an undiluted bed of the same shaped catalyst bodies.

14. A process as claimed in claim 13, wherein the proportion by weight of the shaped diluent bodies in the homogeneous mixture is from 10 to 40% by weight.

15. A process as claimed in claim 13, wherein the homogeneous mixture extends to a length of from 20 to 40% of the total length of the first fixed catalyst bed.

16. A process as claimed in claim 15, wherein the proportion by weight of shaped diluent bodies in the homogeneous mixture is from 20 to 40% by weight.

17. A process as claimed in claim 1, wherein the second fixed catalyst bed in the flow direction of the reaction gas mixture is structured as follows:
   to a length of from 10 to 60% of the total length of the second fixed catalyst bed, a homogeneous mixture of shaped catalyst bodies and shaped diluent bodies and then, up to the end of the length of the second fixed catalyst bed, an undiluted bed of the same shaped catalyst bodies.

18. A process as claimed in claim 17, wherein the proportion by weight of shaped diluent bodies in the homogeneous mixture of the second fixed catalyst bed is from 10 to 50% by weight.

19. A process as claimed in claim 17, wherein the homogeneous mixture of the second fixed catalyst bed extends to a length of from 20 to 40% by weight of the total length of the second fixed catalyst bed.

20. A process as claimed in claim 19, wherein the proportion by weight of shaped diluent bodies in the homogeneous mixture of the second fixed catalyst bed is from 20 to 45% by weight.

21. A process as claimed in claim 1, wherein the first reaction stage and the second reaction stage are carried out in a common tube bundle reactor.

22. A process as claimed in claim 1, wherein the first reaction stage and the second reaction stage are carried out in two tube bundle reactors connected in series.

23. A process as claimed in claim 21, wherein the reaction temperature in the first reaction stage is from 300 to 380° C. and that in the second reaction stage is from 220 to 310° C.

24. A process as claimed in claim 14, wherein the homogeneous mixture extends to a length of from 20 to 40% of the total length of the first fixed catalyst bed.

25. A process as claimed in claim 18, wherein the homogeneous mixture of the second fixed catalyst bed extends to a length of from 20 to 40% by weight of the total length of the second fixed catalyst bed.

26. A process as claimed in claim 22, wherein the reaction temperature in the first reaction stage is from 300 to 380° C. and that in the second reaction stage is from 220 to 310° C.

27. A partially oxidized mixture of the starting gas mixture 1 obtained by the process as claimed in claim 1.

* * * * *